United States Patent [19]

Hsu et al.

[11] Patent Number: 4,478,752
[45] Date of Patent: Oct. 23, 1984

[54] PROCESS FOR OXIDIZING PHENOL TO P-BENZOQUINONE

[75] Inventors: Chao-Yang Hsu, Media; James E. Lyons, Wallingford, both of Pa.

[73] Assignee: Sun Tech, Inc., Philadelphia, Pa.

[21] Appl. No.: 423,984

[22] Filed: Sep. 27, 1982

Related U.S. Application Data

[63] Continuation-in-part of Ser. No. 284,893, Jul. 20, 1981, abandoned.

[51] Int. Cl.$^3$ .............................................. G07C 50/04
[52] U.S. Cl. ................................................ 260/396 R
[58] Field of Search ...................... 260/396 R; 252/441

[56] References Cited

U.S. PATENT DOCUMENTS

| | | | |
|---|---|---|---|
| 3,210,384 | 10/1965 | Hay | 260/396 R |
| 3,213,114 | 10/1965 | Braxton, Jr. et al. | 260/396 R |
| 3,870,731 | 3/1975 | Hutchings | 260/396 R |
| 3,987,068 | 10/1976 | Reilly | 260/396 R |
| 4,208,339 | 6/1980 | Costantini et al. | 260/396 R |

FOREIGN PATENT DOCUMENTS 15221   3/1980   European Pat. Off. ............ 260/396

*Primary Examiner*—Glennon H. Hollrah
*Assistant Examiner*—Raymond Covington
*Attorney, Agent, or Firm*—J. Edward Hess; Donald R. Johnson; Patrick C. Baker

[57] ABSTRACT

In the process of oxidizing phenol to p-benzoquinone with a bivalent copper ion catalyst, the improvement of promoting the catalyst with a base to obtain improved conversion and/or selectivity. The preferred bases used are alkali metal hydroxides and phenates and secondary and tertiary lower alkyl amines.

21 Claims, No Drawings

PROCESS FOR OXIDIZING PHENOL TO P-BENZOQUINONE

This is a continuation-in-part of Ser. No. 284,893 filed July 20, 1981 now abandoned.

It is known in the art to oxidize phenol to p-benzoquinone with oxygen in the presence of a copper ion catalyst and such a process is disclosed in U.S. Pat. No. 3,987,068. In that disclosure the oxidation is carried out in a nitrile solvent using a complex formed from the copper catalyst and the solvent and the operating conditions are said to be at temperatures of from about 0° to 100° C. and a partial pressure of oxygen of from about 7 to 200 (preferably 14 to 100) atmospheres. As pointed out in U.S. Pat. No. 3,987,068, yield of quinone product increases with increased partial pressure of oxygen and it appears from the data therein to require partial pressures of oxygen above about 100 atmospheres in order to achieve conversions of phenol to p-benzoquinone on the order of about 75%. Such pressures are too high to be useful in an economical commercial process because they require special equipment of high capital cost.

U.S. Pat. No. 3,870,731 relates to the oxidation of phenols to benzoquinones in the presence of copper salts as catalysts where the catalyst is promoted with thiocyanate, cyanate, cyanide and halogen ions. In such reactions a solvent such as water is disclosed and other polar solvents soluble or miscible with water may be used. Such solvents are exemplified as certain amides, alcohols, and sulfoxides. It is also gratuitously stated that any of the various solvents may be used alone or in combination with water in any desired ratio.

U.S. Pat. No. 4,208,339 discloses a process for the preparation of p-benzoquinone by oxidation of phenol in the presence of cuprous or cupric ions in the presence of a metal in the metallic form in a nitrile, amide, alcohol or sulfoxide solvent. Reaction rate is said to be increased by including an alkali metal or alkaline earth metal halide.

It has now been found that the copper catalyzed process for oxidation of phenol to p-benzoquinone can be significantly improved so as to enable operation at lower, commercially useful pressures and still achieve an improved conversion and/or improved selectivity to product. In accord with the invention, such objectives are achieved by conducting the oxidation of phenol in the presence of a divalent copper ion catalyst (e.g. $Cu^{++}$) which is promoted with a base wherein the molar ratio of the base to the copper catalyst is no greater than about 2.0.

In carrying out the process of the invention conventional temperature conditions, solvent systems and a choice of divalent (i.e., cupric) copper catalyst may be used. Thus, a temperature of from about 20° to about 100° C. (preferably about 50° to 75° C.) and a nitrile solvent, preferably acetonitrile, is usually employed. The copper catalyst will be preferably a copper II halide, preferably chloride, although nitrate is operable and mixtures of such salts also may be used. However, other copper II salts such as acetates, sulfates, benzoates, carbonates, phosphates, and bisulfates have been found not to be effective catalysts for the reaction. It has also been found that when a monovalent copper catalyst is used, the alkali metal base is not effective in enhancing rate of reaction or selectivity to benzoquinone product. The base used in the process of the invention can be either inorganic or organic and can be very weak such as sodium acetate or very strong such as sodium hydroxide. Specific base promoters which may be used will include the alkali metal bases such as those of the Group I metals e.g., lithium, sodium, potassium, cesium and rubidium and the base will be preferably a hydroxide. Lithium, sodium and potassium hydroxides are preferred, but carbonates and weak alkali metal bases such as acetates, phenolates, methylates and the like are also useful. Other useful bases useful as promotors are the group of secondary and tertiary lower alkyl amines (e.g. $C_1$ to $C_4$ alkyl amines) such as dimethylamine, diethylamine (DEA), dibutylamine and trimethylamine, tripropylamine, triethylamine (TEA) and the like. As indicated above, the reaction can be carried out at moderate pressures and such pressures will generally be between about 100 and about 500 psig partial pressure of oxygen, preferably between about 200 and 400 psig. Mixtures of oxygen and nitrogen, air alone, or oxygen alone may be used, but preferably mixtures of oxygen and nitrogen such as air will be employed as the oxygenating medium.

It is of interest to note that the base promoters are not effective with monovalent copper iron (e.g. $Cu^+$) catalysts. It has also been found that when the mole ratio of the base promoter to copper catalyst used exceeds about 2.0 the effect of the promoter is significantly reduced. The preferred ratio of promoter to copper is generally 1.0 to 2.0.

A still further improvement in selectivity to benzoquinone is obtained when the oxidation method of this invention is carried out in the presence of water. The amount of water which imparts this improvement need not be large and, in fact, any amount less than about 10% by volume of the reaction solution is quite effective. More than about 10% should be avoided because conversion is lowered.

In order to further illustrate the invention, the following examples are given:

EXAMPLE I

A solution of phenol in 5 ml. of acetonitrile which was agitated in a magnetically stirred mini-autoclave under an initial total pressure of 750 psig was oxidized over a three hour period with a mixture of 40% (vol.) oxygen and 60% nitrogen in the presence of a $CuCl_2$ catalyst. The reaction parameters and results obtained are shown in the following Table I.

TABLE I

EFFECT OF A GROUP IA BASE ON THE COPPER(II) CHLORIDE CATALYZED OXIDATION OF PHENOL

| Catalyst | MMoles Cat. | Base | MMoles Base | MMoles Phenol | Temp. (°C.) | Time. (Min.) | % Selectivity To PBQ[1] | % Conversion To Phenol | % Yield to PBQ[1] |
|---|---|---|---|---|---|---|---|---|---|
| $CuCl_2$ | 0.55 | — | — | 3.81 | 65 | 180 | 42 | 85 | 36 |
| $CuCl_2$ | 0.55 | LiOH | 0.55 | 7.36 | 65 | 180 | 50 | 98 | 49 |
| $CuCl_2$ | 0.55 | LiOH | 0.55 | 7.36 | 65 | 180 | 46 | 98 | 45 |

TABLE I-continued

EFFECT OF A GROUP IA BASE ON THE COPPER(II) CHLORIDE CATALYZED OXIDATION OF PHENOL

| Catalyst | MMoles Cat. | Base | MMoles Base | MMoles Phenol | Temp. (°C.) | Time. (Min.) | % Selectivity To PBQ[1] | % Conversion To Phenol | % Yield to PBQ[1] |
|---|---|---|---|---|---|---|---|---|---|
| CuCl$_2$ | 0.55 | LiOH | 0.55 | 7.36 | 65 | 180 | 48 | 98 | 47 |

[1]PBQ = p-Benzoquinone

The data in Table I clearly shows the formation of more PBQ in the presence of the alkali metal promoter than in its absence.

EXAMPLE II

Following the experimental details of Example I with 0.55 mmoles of catalyst, additional runs were carried out. In some runs water was present during the oxidations. Table II shows the reaction parameters with numerous agents present and also shows the results obtained.

should be understood, of course, that an improvement in selectivity is of much greater significance than improved conversion since conversion can always be increased by recycling the unreacted reagents. Comparative runs 13 and 14 show that when the mole ratio of promoter to catalyst is higher than about 2.0, selectivity is reduced. Comparative runs 2, 9 and 10 show alkali metal halides to be relatively ineffective to increase selectivity without or with water. Table II also illustrates the use of alkali metal acetates, phenolates, carbonates and methylates as being effective to increase

TABLE II

OXIDATION OF PHENOL TO PBQ USING Cu(II)

| RUN NO. | PROMOTER | PROMOTER (MMOLES) | MODIFIER | MODIFIER (MMOLES) | PHENOL USED (MMOLES) | CONVERSION OF PHENOL (%) | SELECTIVITY to PBQ (%) |
|---|---|---|---|---|---|---|---|
| 1 | — | — | — | — | 4 | 83 | 39 |
| 2 | — | — | — | — | 8 | 73 | 49 |
| 3 | — | — | — | — | 12 | 32 | 51 |
| 4 | — | — | — | — | 16 | 32 | 55 |
| 5 | — | — | — | — | 20 | 23 | 62 |
| 6 | — | — | — | — | 34 | 37 | 16 |
| 7 | — | — | — | — | — | — | — |
| 8 | — | — | Water | 14.0 | 7.5 | 35 | 48 |
| 9 | LiCl | 0.55 | — | — | 7.5 | 99 | 52 |
| 10 | LiCl | 0.55 | Water | 14.0 | 7.5 | 87 | 54 |
| 11 | LiOH | 0.55 | — | — | 7.5 | 98 | 48 |
| 12 | LiOH | 0.55 | Water | 14.0 | 7.5 | 60 | 68 |
| 13 | LiOH | 1.10 | Water | 14.0 | 7.5 | 46 | 74 |
| 14 | LiOH | 1.65 | Water | 14.0 | 7.5 | 13 | 27 |
| 15 | KOH | 0.55 | Water | 14.0 | 7.5 | 58 | 61 |
| 16 | KOH | 1.10 | Water | 28.0 | 7.5 | 42 | 67 |
| 17 | LiOAc | 0.55 | — | — | 7.5 | 94 | 59 |
| 18 | NaOAc | 0.55 | — | — | 7.5 | 92 | 58 |
| 19 | KOAc | 0.55 | — | — | 7.5 | 83 | 51 |
| 20 | RbOAc | 0.55 | — | — | 7.5 | 66 | 65 |
| 21 | Na$_2$CO$_3$ | 0.55 | — | — | 7.5 | 97 | 55 |
| 22 | NaOPh | 0.55 | — | — | 7.5 | 98 | 55 |
| 23 | NaOPh | 1.10 | — | — | 7.5 | 68 | 57 |
| 24 | LiOPh | 0.55 | — | — | 7.5 | 95 | 49 |
| 25 | LiOPh | 1.10 | — | — | 7.5 | 92 | 49 |
| 26 | LiOMe | 0.55 | — | — | 7.5 | 98 | 50 |
| 27 | LiOMe | 0.55 | — | — | 7.5 | 94 | 37 |
| 28 | NaOMe | 0.55 | — | — | 7.5 | 95 | 52 |
| 29 | NaOMe | 1.10 | — | — | 7.5 | 79 | 37 |

As can be seen from the data in Table II, the presence of promoter and water contributes to improved selectivity. Of particular interest are runs 2, 8, 11, 12 and 13. Comparison of runs 2 and 8 show that the addition water to a system without promoter actually reduces conversion. Comparison of runs 2 and 11 show improved conversion with the alkaline promoter. Comparison of runs 11 and 12 show that when promoter is present, the presence of water improves selectivity. It conversion of phenol in the process of the invention.

EXAMPLE III

A solution of phenol in 5 ml. of acetonitrile containing the catalyst and promoter was oxidized with a mixture of 40% oxygen and 60% nitrogen in a glass-lined, magnetically stirred reactor. The reactor was heated to 65° C. and the reaction time was three hours. The following Table III gives the data and results obtained:

TABLE III

THE EFFECT OF AQUEOUS ALKALI ON THE SELECTIVITY OF P-BENZOQUINONE (PBQ) AND ON THE QUANTITY OF CHLOROPHENOLS FORMED DURING THE COPPER-CATALYZED OXIDATION OF PHENOL.

| CATALYST | (MMOLES) | BASE | (MMOLES) | H$_2$O (MMOLES) | PHENOL CONV. (%) | PBQ SEL. (%) | CHLOROPHENOL YIELD (%) |
|---|---|---|---|---|---|---|---|
| CuCl$_2$ | (0.55) | — | (0.0) | 0 | 65 | 44 | 3.1 |
| CuCl$_2$ | (0.55) | — | (0.0) | 7 | 50 | 52 | 3.9 |
| CuCl$_2$ | (0.50) | NaOH | (0.25) | 7 | 83 | 56 | 0.2 |

TABLE III-continued

THE EFFECT OF AQUEOUS ALKALI ON THE SELECTIVITY OF P-BENZOQUINONE (PBQ) AND ON THE QUANTITY OF CHLOROPHENOLS FORMED DURING THE COPPER-CATALYZED OXIDATION OF PHENOL.

| CATALYST | (MMOLES) | BASE | (MMOLES) | $H_2O$ (MMOLES) | PHENOL CONV. (%) | PBQ SEL. (%) | CHLOROPHENOL YIELD (%) |
|---|---|---|---|---|---|---|---|
| $CuCl_2$ | (0.50) | NaOH | (0.50) | 14 | 35 | 71 | 1.1 |
| $CuCl_2$ | (0.55) | KOH | (0.55) | 14 | 58 | 61 | — |
| $CuCl_2$ | (0.55) | LiOH | (0.55) | 14 | 60 | 68 | 1.3 |
| $CuCl_2$ | (0.55) | LiOH | (1.01) | 14 | 46 | 74 | — |

As can be seen from the above data another advantage of the process is the very low level chlorophenol by-products formed when the aqueous alkali metal base promoter system is used.

EXAMPLE IV

A solution of 16 mmole of phenol in 5 ml. of acetonitrile containing 0.55 mmole of catalyst and 0.55 mmole of the amine modifier was agitated in a magnetically stirred mini-autoclave under an initial total pressure of 750 psig and was oxidized over a three-hour period with a mixture of 40% (vol.) oxygen and 60% nitrogen. The reaction parameters and results obtained are shown in the following Table IV.

TABLE IV

EFFECT OF ALKYL AMINES ON COPPER-CATALYZED OXIDATION OF PHENOL TO p-BENZOQUINONE

| RUN # | CATALYST | MODIFIER[a] | CONV.[b] (%) | SEL.[c] (%) |
|---|---|---|---|---|
| 1 | $CuCl_2$ | — | 32 | 55 |
| 2 | $CuCl_2$ | TEA | 63 | 70 |
| 3 | $CuCl_2$ | DEA | 55 | 70 |
| 4 | $CuCl_2$ | LiOPh | 62 | 90 |
| 5 | CuCl | — | 47 | 61 |
| 6 | CuCl | TEA | 50 | 21 |
| 7 | CuCl | DEA | 41 | 64 |

[a]TEA = Triethylamine; DE = Diethylamine; LiOPh = Lithium Phenoxide
[b]Mole % Phenol Converted
[c]Selectivity to p-Benzoquinone

We claim:

1. In the process of oxidizing phenol to benzoquinone in a nitrile solvent with a bivalent copper salt catalyst selected from the group of halides and nitrates the improvement of obtaining increased selectivity by promoting the catalyst with a base wherein the mole ratio of the base to the copper catalyst is from 1:2 to about 2:1.

2. The process of claim 1 wherein the catalyst is cupric chloride.

3. The process of claim 1 wherein the process is carried out in the presence of water in an amount less than about 10% by volume of the reaction solution containing said phenol, catalyst and base in said solvent.

4. The process of claim 3 where in the catalyst is cupric chloride and the base is an alkali metal hydroxide.

5. The process of claim 1 wherein the catalyst is cupric nitrate.

6. The process of claim 4 wherein the base is lithium hydroxide.

7. The process of claim 4 wherein the base is lithium phenoxide.

8. The process of claim 1 wherein the base is a secondary or tertiary lower alkyl amine.

9. In the process of oxidizing phenol to p-benzoquinone with a bivalent copper salt catalyst selected from the group of halides and nitrates in an acetonitrile solvent system, the improvement of obtaining increased selectivity which comprises promoting the catalyst with an alkali metal base wherein the mole ratio of the base to the copper catalyst is from 1:2 to about 2:1.

10. The process of claim 9 wherein the catalyst is cupric chloride.

11. The process of claim 9 wherein the process is carried out in the presence of water in an amount less than about 10% by volume of the reaction solution containing said phenol, catalyst and base in said solvent.

12. The process of claim 11 wherein the catalyst is cupric chloride.

13. The process of claim 11 wherein the base is an alkali metal hydroxide and the catalyst is cupric chloride.

14. The process of claim 12 wherein the base is lithium hydroxide.

15. The process of claim 12 wherein the base is lithium phenoxide.

16. The process of claim 12 wherein the base is potassium hydroxide.

17. The process of claim 12 wherein the base is sodium hydroxide.

18. In the process of oxidizing phenol to p-benzoquinone with a bivalent copper salt catalyst selected from the group of halides and nitrates in an acetonitrile solvent system, the improvement of obtaining increased selectivity which comprises promoting the catalyst with a secondary or tertiary lower alkyl amine wherein the mole ratio of the amine to the copper catalyst is from 1:2 to about 2:1.

19. The process of claim 18 wherein the catalyst is cupric chloride.

20. The process of claim 18 wherein the amine is diethylamine and the catalyst is cupric chloride.

21. The process of claim 18 wherein the amine is triethylamine and the catalyst is cupric chloride.

* * * * *